(12) United States Patent
Chesbrough et al.

(10) Patent No.: US 6,575,991 B1
(45) Date of Patent: Jun. 10, 2003

(54) APPARATUS FOR THE PERCUTANEOUS MARKING OF A LESION

(75) Inventors: Richard M. Chesbrough, Bloomfield Hills, MI (US); Steven E. Field, Grand Rapids, MI (US); Ryan L. Goosen, Coopersville, MI (US); Jeff Zerfas, Kalamazoo, MI (US); Richard E. Davis, Grand Rapids, MI (US)

(73) Assignee: Inrad, Inc., Grand Rapids, MI (US)

( * ) Notice: Subject to any disclaimer, the term of this patent is extended or adjusted under 35 U.S.C. 154(b) by 276 days.

(21) Appl. No.: 09/596,160

(22) Filed: Jun. 16, 2000

Related U.S. Application Data

(60) Provisional application No. 60/139,580, filed on Jun. 17, 1999.

(51) Int. Cl.[7] .............................................. A61B 17/34
(52) U.S. Cl. ............................................................ 606/185
(58) Field of Search ............................... 606/185, 167, 606/170, 181, 184; 600/564, 567, 562, 7; 604/63, 57, 46, 73, 264; 222/153.01, 41

(56) References Cited

U.S. PATENT DOCUMENTS

| | | | |
|---|---|---|---|
| 4,401,124 A | * 8/1983 | Guess et al. | 128/660 |
| 4,682,606 A | * 7/1987 | DeCaprio | 128/754 |
| 5,195,540 A | * 3/1993 | Shiber | 128/898 |
| 5,242,759 A | 9/1993 | Hall | |
| 5,354,623 A | 10/1994 | Hall | |
| 5,417,708 A | 5/1995 | Hall et al. | |
| 5,853,366 A | 12/1998 | Dowlatshahi | |
| 6,056,700 A | 5/2000 | Burney et al. | |
| 6,142,955 A | * 11/2000 | Farascioni et al. | 600/562 |
| 6,161,034 A | * 12/2000 | Burbank et al. | 600/431 |
| 6,213,957 B1 | * 4/2001 | Milliman et al. | 600/566 |
| 6,228,055 B1 | * 5/2001 | Foerster et al. | 604/116 |
| 6,241,687 B1 | * 6/2001 | Voegele et al. | 600/566 |
| 6,261,243 B1 | * 7/2001 | Burney et al. | 600/564 |
| 6,336,904 B1 | * 1/2002 | Nikolchev | 600/562 |
| 6,371,904 B1 | * 4/2002 | Sirimanne et al. | 600/3 |

FOREIGN PATENT DOCUMENTS

| | | |
|---|---|---|
| DE | 10 29 528 B | 5/1958 |
| EP | 0 769 280 A | 4/1997 |
| EP | 0 769 281 A | 4/1997 |
| WO | WO 96 08208 A | 3/1996 |
| WO | WO 00 28554 A | 5/2000 |

OTHER PUBLICATIONS

Press release for Biopsys Ethicon Endo–Surgery (Europed) GmbH, The Mammotone Vacuum Biopsy System. From http://www.medicine–news.com. 3 pages.

Steps in MMOTOME Surgical Procedure. From http://www.jnjgateway.com. 3 pages.

New Minimally Invasive Breast Biopsy Device Receives Marketing Clearance in Canada. From http://www.jun.com. 4 pages.

Mammotome Hand Held Receives FDA Marketing Clearance for Minimally Invasive Breast Biopsies. From http://www.jnj.com. 5 pages.

(List continued on next page.)

Primary Examiner—John J. Calvert
Assistant Examiner—Alissa L Hoey
(74) Attorney, Agent, or Firm—McGarry Bair PC

(57) ABSTRACT

A biopsy marking apparatus for placing a radiopaque marker at the location of a percutaneous biopsy. The biopsy marking apparatus comprises an introducer in combination with a radiopaque marker. The introducer ejects the radiopaque marker at the location of the biopsy. The introducer is configured to completely eject the radiopaque marker and prevent it from being subsequently drawn into the introducer as the introducer is removed from the biopsied tissue mass. The radiopaque marker has enhanced radiopaque characteristics and enhanced non-migration characteristics.

60 Claims, 10 Drawing Sheets

OTHER PUBLICATIONS

Percutaneous Removal of Malignant Mammographic Lesions at Stereotactic Vacuum–assisted Biopsy. From the Departments of Radiology, Pathology, and Surgery; Memorial Sloan–Kettering Cancer Center; from the 1997 RSNA scientific assembly. vol. 206, No. 3, pp. 711–715.

The Mammotome Breast Biopsy System. From http://www.breastcareinfo.com. 6 pages.

Embolization and Occlusion. From www.cookgroup.com. 6 pages.

* cited by examiner

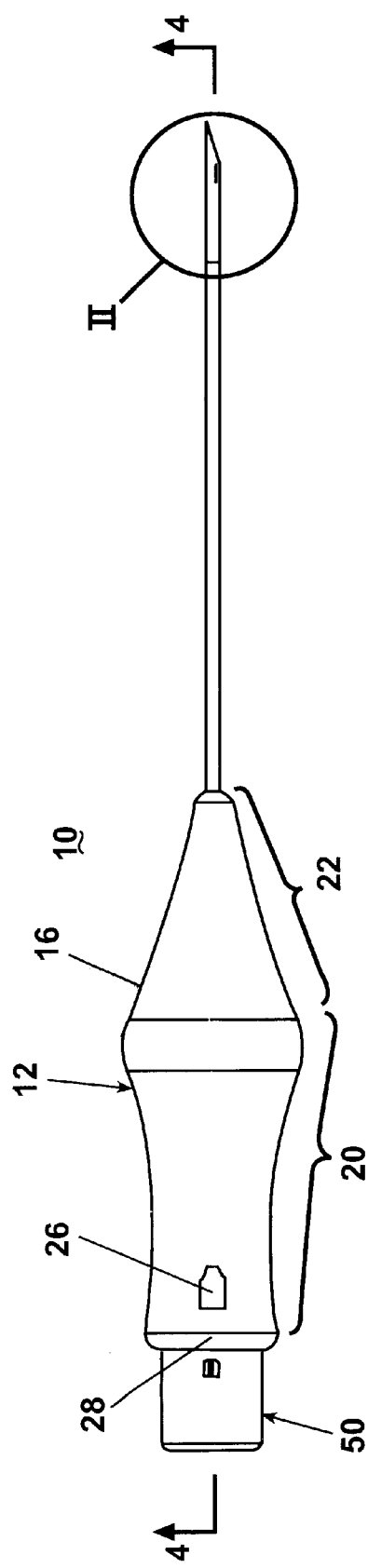
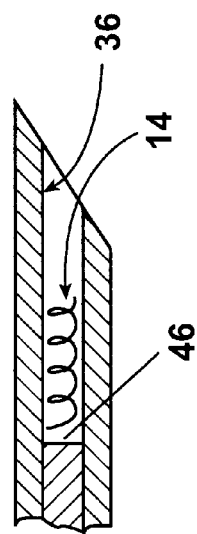
Fig. 1
Fig. 2

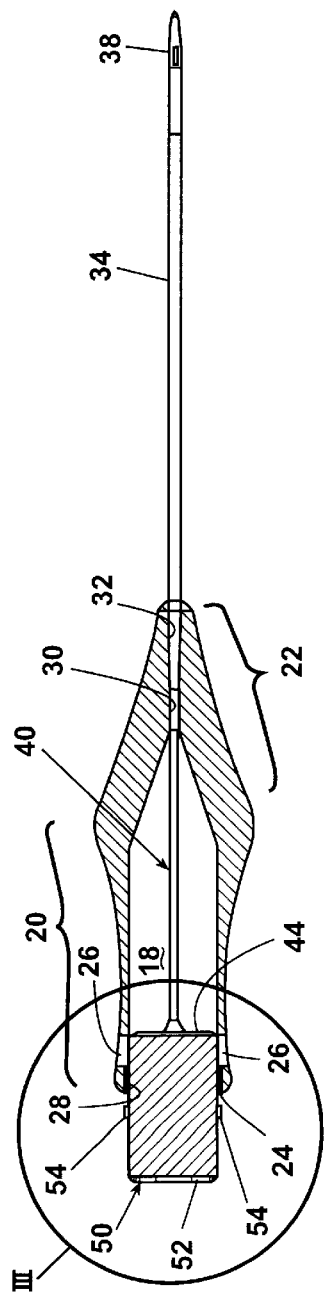
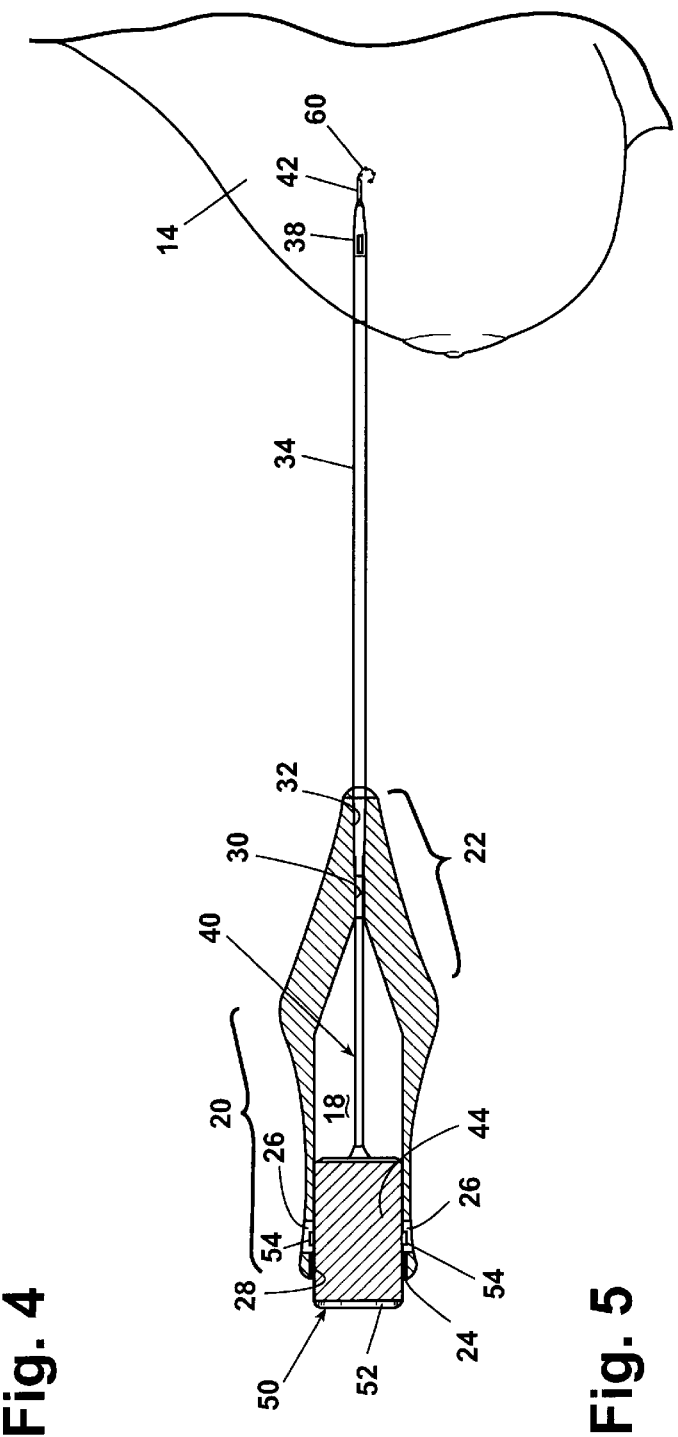

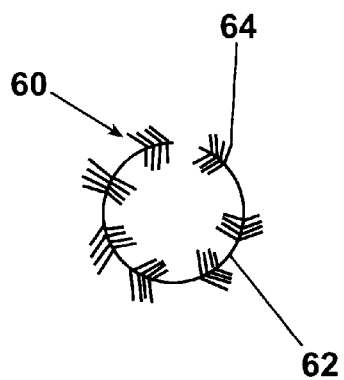
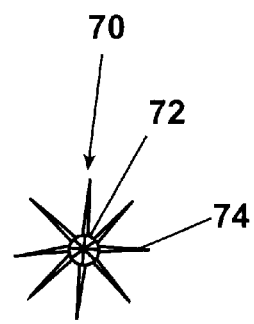
Fig. 6     Fig. 7
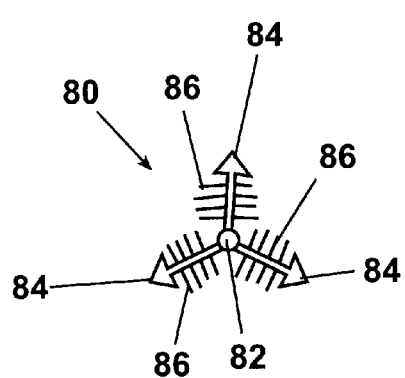
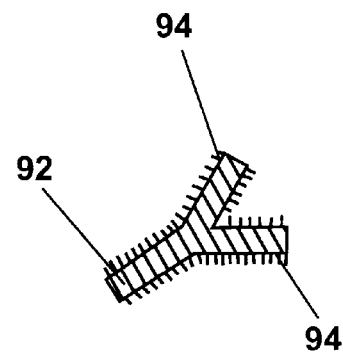
Fig. 8     Fig. 9

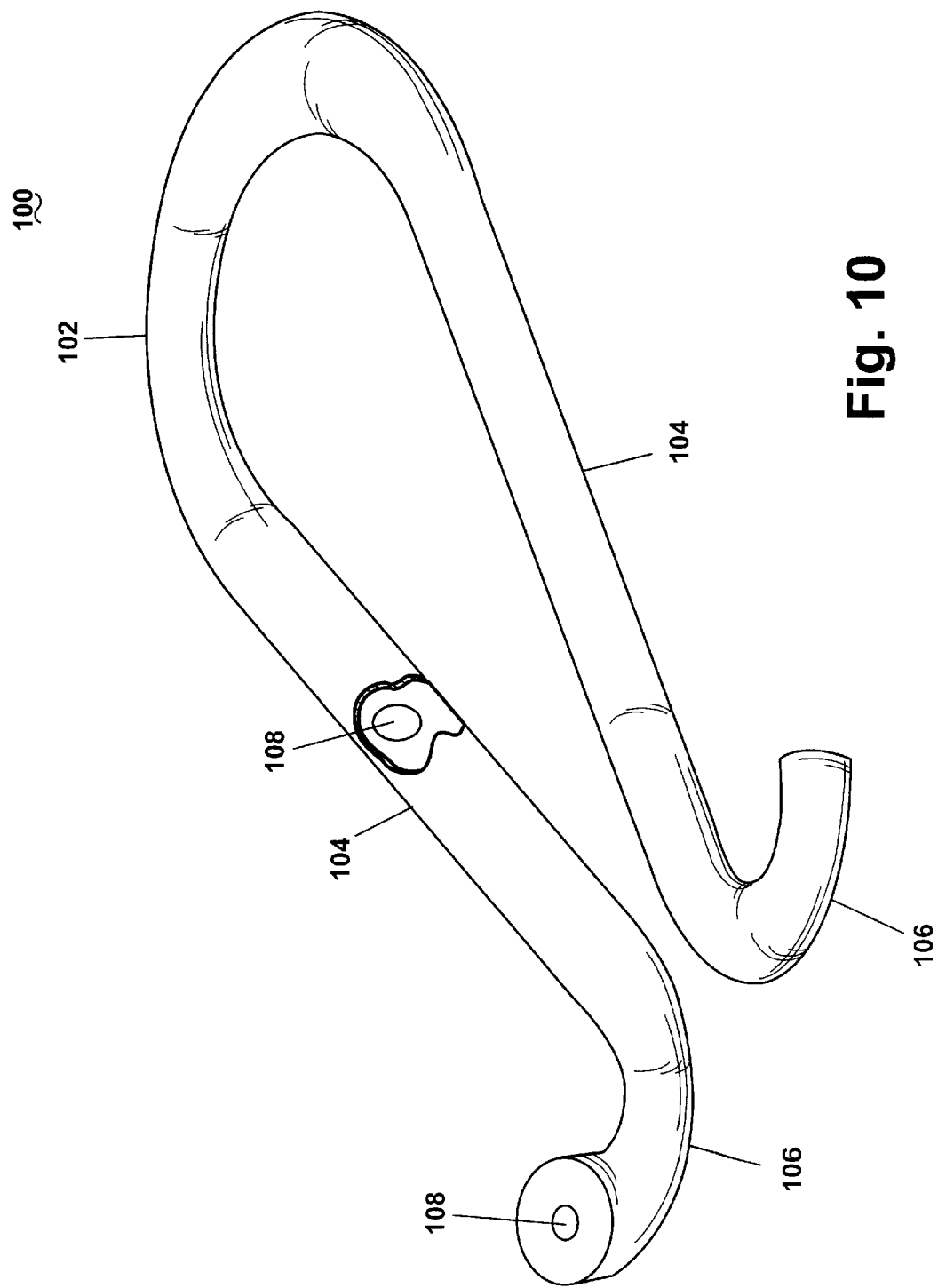

APPARATUS FOR THE PERCUTANEOUS MARKING OF A LESION

RELATED APPLICATION

This claims the priority of U.S. provisional patent application Serial No. 60/139,580, filed Jun. 17, 1999.

BACKGROUND OF THE INVENTION

1. Field of the Invention

This invention relates generally to an apparatus for the percutaneous positioning of a radiopaque marker for identifying the location of a lesion in a stereotactic biopsy procedure. More particularly, the invention relates to an introducer having a hollow cannula in combination with a movable stylet and a radiopaque marker disposed within the cannula and ejected from it by movement of the stylet.

2. Related Art

Tissue biopsies are commonly performed on many areas and organs of the body where it is desirable to ascertain whether or not the biopsied tissue is cancerous. Often, a lesion or other tissue to be biopsied is identified through use of an imaging technique such as a computerized axial tomography (CAT) scan, ultrasonography, and mammography.

One problem commonly encountered, especially in breast biopsies, is that the lesion is so small that the biopsy reduces its size to the extent that it is no longer visible by the imaging method employed. In such circumstances, it is desirable to place a radiopaque marker at the site of the biopsy to enable the medical practitioner subsequently to locate the lesion quickly and accurately in the event complete removal of the affected tissue is indicated. This problem is currently met by placing a radiopaque marker at the biopsy area by means of a cannula or similar device housing the marker.

More particularly, one of the markers heretofore in use is a staple-type clip. The clip is introduced through a large-diameter cannula, specifically one of 11 gauge.

Some practitioners employ an embolization coil as a marker. This requires them to find a cannula or hollow needle of a size to receive the coil and some means to force the coil through the needle, all the while trying to keep these components together and sterile.

Prior devices for marking a biopsy area have several other disadvantages. A significant disadvantage is that the marker is not always completely ejected from the cannula or can be drawn back into or toward the cannula by the vacuum created upon the withdrawal of the cannula, which results in the marker being moved from the intended site, leading to inaccurate identification of the location of the biopsy area. A second major disadvantage is that current markers have a tendency to migrate within the tissue, also causing error in determining the biopsy location.

SUMMARY OF THE INVENTION

The present invention provides a biopsy marking apparatus for the percutaneous placement of a marker at a biopsy site in a tissue mass to facilitate subsequent determination of the location of the biopsy site. The biopsy marking apparatus comprises an introducer having a handle to be grasped by a user, a cannula, a stylet, and a radiopaque marker. The cannula has a proximal end mounted to the handle and a distal end defining an insertion tip. The stylet is slidably received within the cannula for movement between a ready position in which a distal end of the stylet is spaced inwardly from the cannula tip to form a marker recess between the distal end of the stylet and the cannula tip, and an extended position in which the distal end of the stylet extends at least to the cannula tip to effectively fill the marker recess.

A plunger is movably mounted to the handle and operably engages the stylet, the plunger being movable between a first position and a second position for moving the stylet between the ready position and the extended position.

A latch is provided for fixing the stylet in the extended position to prevent retraction of the stylet from that position.

A radiopaque marker is disposed within the marker recess, whereby, when the plunger is moved between the first and second positions, the stylet is moved from the ready to the extended position to eject the radiopaque marker from the marker recess, and the latch fixes the stylet in the extended position to prevent the return of the marker to the marker recess.

The latch preferably comprises a detent on either the plunger or the handle and a catch on the other, the catch being receivable within the detent as the plunger is moved from the first to the second position.

In another aspect, the invention also provides a radiopaque marker having a marker body and an anchor extending away from the body for fixing the location of the radiopaque marker in a tissue mass by the tissue mass prolapsing about the anchor. Preferably, the body has an interior hollow portion forming an air trap to enhance the ultrasound characteristic of the radiopaque marker.

Other features and advantages of the invention will be apparent from the ensuing description in conjunction with the accompanying drawings.

BRIEF DESCRIPTION OF THE DRAWINGS

In the drawings:

FIG. 1 is a plan view of an introducer used to place a radiopaque marker at a biopsy location in accordance with the invention;

FIG. 2 is an enlarged sectional view of the area II of FIG. 1, illustrating the position of a radiopaque marker within the introducer prior to ejection;

FIG. 4 is a sectional view taken along line 4—4 of FIG. 1 and illustrating the introducer in a ready condition;

FIG. 5 is a sectional view taken along line 4—4 of FIG. 1 and illustrating the introducer in a discharged condition;

FIG. 6 is an enlarged view of a first embodiment of a radiopaque marker according to the invention;

FIG. 7 is an enlarged view of a second embodiment of a radiopaque marker according to the invention;

FIG.8 is an enlarged view of a third embodiment of a radiopaque marker according to the invention;

FIG. 9 is an enlarged view of a fourth embodiment of a radiopaque marker according to the invention;

FIG. 10 is a partially broken away perspective view, greatly enlarged, of a fifth embodiment of a radiopaque marker according to the invention;

DETAILED DESCRIPTION

Figure 3:
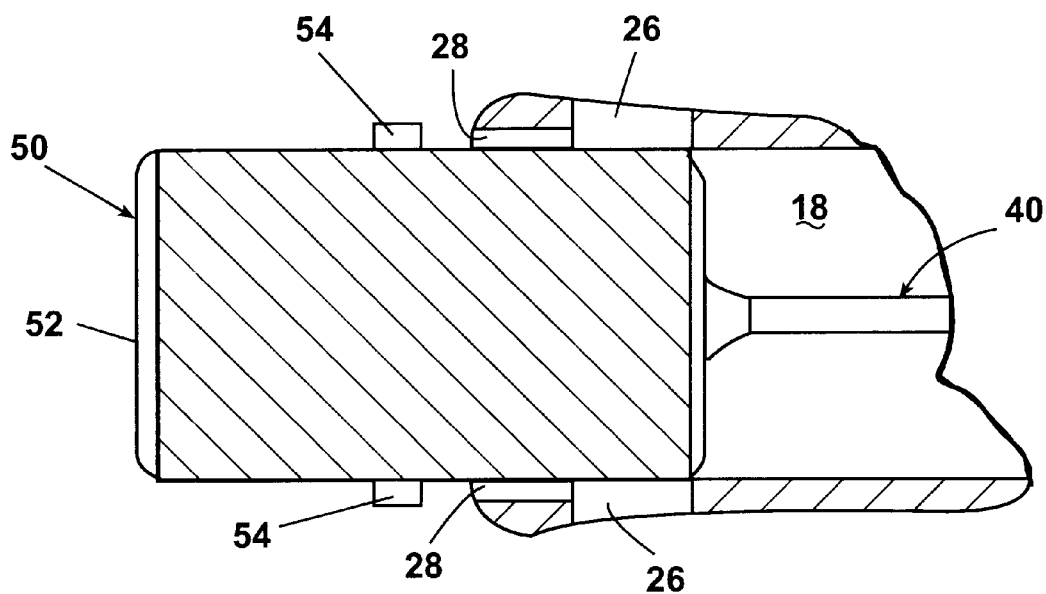
FIG. 3 is an enlarged sectional view of the area III of FIG. 1, illustrating the arrangement of a handle, a plunger, and a stylet of the introducer.
Figure 11:
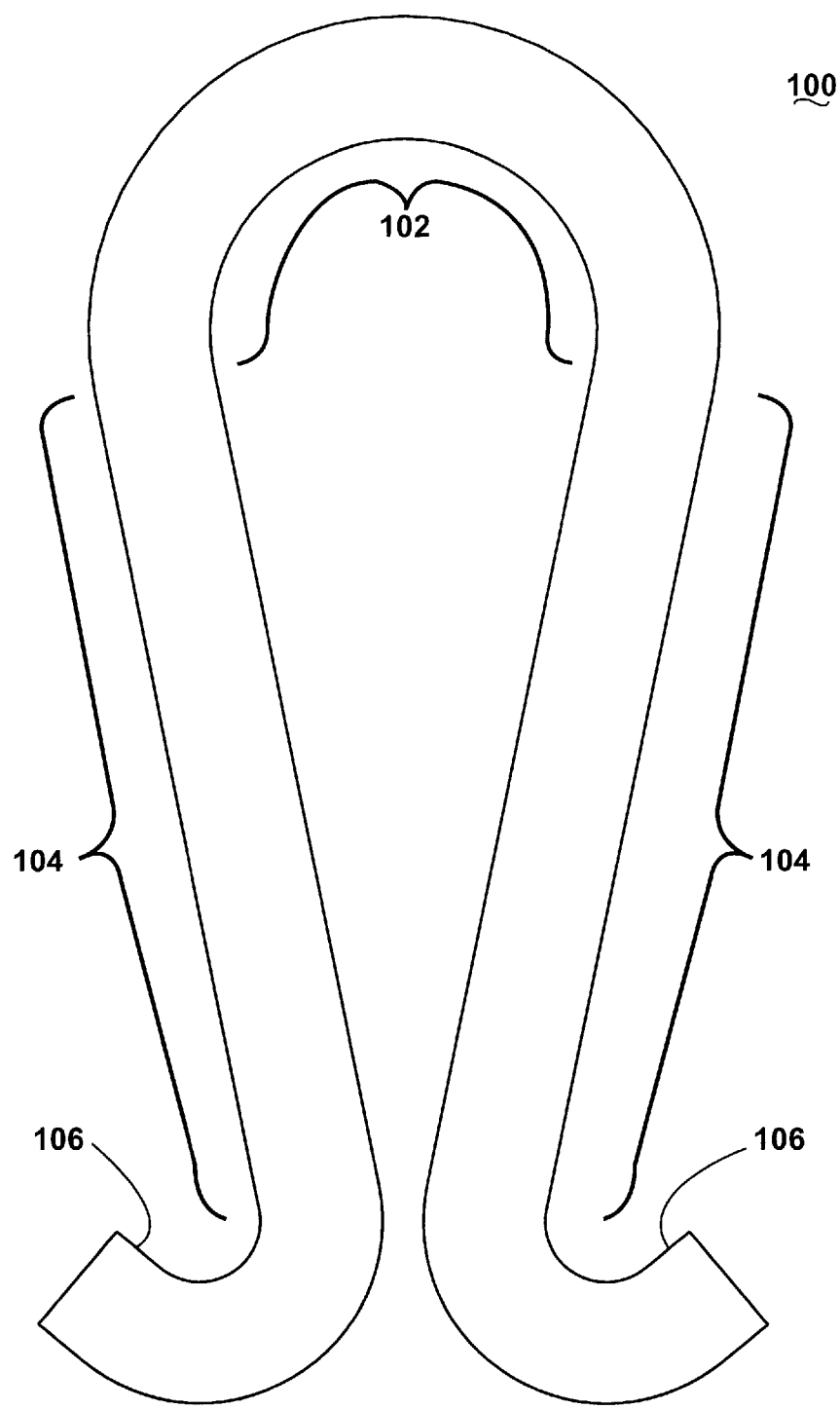
FIG. 11 is a plan view of the radiopaque marker of FIG. 10.

FIGS. 1 to 4 illustrate a biopsy marking apparatus 10 according to the invention, which is capable of the percutaneous placement of a radiopaque marker at the location of a tissue biopsy. The biopsy marking apparatus 10 comprises an introducer 12 and a radiopaque marker 14 (FIG. 2) contained within the introducer 12. The introducer 12 includes a handle 16 having a hollow interior 18. The handle 16 comprises a grip portion 20 from which extends a tapered nose portion 22. The grip portion 20 defines a rear opening 24 that provides access to the hollow interior 18. A pair of detents 26 are formed in the grip portion 20 near the rear opening 24. Channels 28 are formed on the interior surface of the grip portion 20 and extend from the rear opening 24 to the detents 26.

The nose portion 22 comprises a guide passage 30 extending from the tip of the nose portion 22 to the hollow interior 18 of the handle 16. The guide passage 30 decreases in diameter inwardly from the tip of the nose portion to form a cannula seat 32. Alternatively, the diameter of the guide passage 30 may be substantially equal to or slightly smaller than the outer diameter of a cannula 34, which in any case is press-fit within the cannula seat 32. As is customary, the cannula is formed with a hollow interior 36 and a sharpened tip 38.

A stylet 40 comprising a shaft 42 and a base 44 is received within the hollow interior 18 of the handle 16 in a manner such that the shaft 42 extends through the guide passage 30 and into the cannula interior 36 and the stylet base lies within the hollow interior 18.

A plunger 50 comprises a cylindrical body 52 from which extend a pair of catches 54 at diametrically opposed positions. The cylindrical body 52 is sized so that it is slidably received within the rear opening 24 of the handle 16, where it is so oriented with respect to the handle that the catches 54 are aligned with the guide channels 28.

It will be recognized that the foregoing construction provides a biopsy marking apparatus which may be preassembled as a unit and prepackaged, all under sterile conditions, thereby affording the practitioner substantially greater convenience and reliability. Such a construction also permits use of a narrower cannula, which may be of 14 gauge or smaller.

In operation, the introducer 12 begins in the ready condition shown in FIG. 4. In this condition, the stylet shaft is received within the cannula but does not extend to the cannula tip 38, thereby forming a marker recess 46 within the cannula 34, the radiopaque marker 14 is disposed within the marker recess 46, and the plunger 50 is in a position relative to the handle 20 in which the catches are outside the handle; that is, they are not received within the detents 26. However, the plunger 50 is so oriented with respect to the handle that the catches 54 are aligned with the guide channels 28.

With the introducer in the ready condition, the cannula is positioned so that its tip is at or near the location of a tissue mass where a biopsy has been taken. Preferably, the cannula tip is positioned by using imaging systems. The cannula tip 38 can be designed for enhanced visibility using common imaging systems, such as CAT scan, ultrasonography and mammography. Suitable cannula tips are disclosed in U.S. Pat. No. 5,490,521, issued Feb. 13, 1996 to R. E. Davis and G. L. McLellan, which is incorporated by reference. Ultrasound enhancement technology is also disclosed in U.S. Pat. No. 4,401,124, issued Aug. 30, 1983 to J. F. Guess, D. R. Dietz, and C. F. Hottinger; and U.S. Pat. No. 4,582,061, issued Apr. 15, 1986 to F. J. Fry.

Once the cannula is positioned at the desired location, the plunger 50 is moved from its first or ready condition as illustrated in FIGS. 1 to 4 to a second or discharged condition in which the catches 54 are received within the detents 26 to lock the plunger 50 in the discharged condition and the stylet shaft extends beyond the cannula tip 38. The catches 50 and detents combine to function as a latch for locking the plunger in the discharged condition. As the plunger 50 is moved from the ready condition to the discharged condition, the plunger 50 drives the stylet base 44 forward to advance the stylet shaft 42 within the cannula interior 36. As the stylet shaft 42 is advanced, the radiopaque marker 14 is ejected from the marker recess 46 through the cannula tip 38 and into the tissue at the biopsy location.

It is preferred that the stylet shaft 42 be sized in a manner such that when the plunger 50 is in the discharged condition the stylet shaft 42 extends beyond the cannula tip 38 to ensure the complete ejection of the radiopaque marker 14 from the marker recess 46. The extension of the stylet shaft 42 beyond the cannula tip 38 also prevents the radiopaque marker 14 from being drawn back into the marker recess upon the removal of the introducer 12 from the tissue mass, which can occur as the tissue mass collapses and is drawn towards and into the cannula by the resilient nature of the tissue mass and the creation of a vacuum by the cannula as it is withdrawn from the tissue.

The rate at which the plunger 50 is moved from the ready condition to the discharged condition is preferably manually controlled by the user to control the rate at which the marker 14 is ejected into the tissue mass. Manual control of the ejection rate of the radiopaque marker provides the user with the ability to adjust the position of the cannula tip as the marker is being ejected and thereby permits additional control of the final location of the marker within the tissue mass. In other words, "on-the-fly" adjustment of the cannula tip during positioning of the marker 14 enables a more accurate placement of the marker.

The biopsy marking apparatus 12 may be placed in a safety condition (not shown) before packaging or use by rotationally orienting the plunger 50 with respect to the handle 16 so that the catches 54 are out of alignment with the guide channels 28, whereby the plunger cannot be depressed or advanced within the handle. It will be apparent that the marking apparatus can be placed in the ready condition previously described simply by rotating the plunger relative to the handle until the catches 54 are aligned with the guide channels 28.

It will also be apparent that the biopsy marking apparatus 10 may incorporate or be fitted with any one of several known trigger devices, some of them spring-loaded, for advancement of the plunger 50. Such a trigger device is disclosed, for example, in U.S. Pat. No. 5,125,413, issued Jun. 30, 1992 to G. W. Baran.

It should be noted that as a variation of the foregoing procedure the cannula employed during the biopsy procedure might be left in place with its tip remaining at the site of the lesion. The introducer 12 of the present invention would then be directed to the site through the biopsy cannula or, alternatively, the marker 14 of the present invention would be introduced to the biopsy cannula and ejected from its tip into the tissue mass by fitting the biopsy cannula to the introducer 12 in place of the cannula 34.

The radiopaque marker 14 used in combination with the introducer 12 to mark the location of the tissue biopsy should not only be readily visible using contemporary imaging techniques but it should not migrate within the tissue from the position in which it is initially placed. FIGS. 6 to 15 disclose various embodiments of radiopaque markers 14 that are highly visible using contemporary imaging techniques and are resistant to migration in the tissue.

FIG. 6 illustrates a first embodiment 60 of a radiopaque marker comprising a coil spring 62 from which extend radiopaque fibers 64. The coil spring 62 is preferably made from platinum or any other material not rejected by the body. The coil spring 62 is wound to effectively form a hollow interior comprising one or more air pockets, which are highly visible using contemporary ultrasound imaging techniques. The radiopaque fibers 64 are preferably made from Dacron, which is also highly visible using current imaging techniques.

The radiopaque marker 60 is highly visible using any of the commonly employed contemporary imagining techniques because of the combination of reflective surfaces formed by the coils, the hollow interior and the air pockets of the coil spring 62, as well as the radiopaque fibers 64.

The coil spring 62 is pre-shaped prior to being loaded into the marker recess 46 so that it tends to form a circular shape as shown in FIG. 6 after it is ejected from the marker recess 46. The circular shape tends to resist migration within the tissue.

FIG. 7 illustrates a second embodiment 70 of a radiopaque marker having a star-burst configuration comprising a core 72 with multiple fingers 74 extending from the core.

FIG. 8 illustrates a third embodiment 80 of a radiopaque marker that is similar to the star-burst marker 70 in that it comprises a core 82 from which extend three fingers 84. Each of the fingers includes radiopaque fibers 86, which are preferably made from Dacron or a similar material.

FIG. 9 illustrates a fourth embodiment 90 of a radiopaque marker having a generally Y-shaped configuration comprising an arm 92 from which extend diverging fingers 94. The arm and fingers 92, 94 are preferably made from a suitable resilient metal such that the fingers can be compressed towards each other and the entire radiopaque marker 90 stored within the marker recess 46 of the cannula. Upon ejection of the marker 90 from the marker recess 46 into the tissue mass, the fingers 94 will spring outwardly to provide the marker 90 with an effectively greater cross-sectional area.

In addition to providing the marker 90 with an effectively greater cross-sectional area, the tips of the fingers 94, together with the free end of the arm 92, effectively form points of contact with the surrounding tissue mass that help to anchor the marker 90 in its release condition to prevent migration through the tissue mass.

FIG. 10 illustrates a fifth embodiment 100 of a radiopaque marker having a wire-form body in a horseshoe-like configuration comprising a rounded bight portion 102 from which extend inwardly tapering legs 104, each of which terminate in curved tips 106. The entire marker 100 preferably has a circular cross section defining a hollow interior 108. The hollow interior provides for the trapping of air within the marker 100 to improve the ultrasound characteristics of the marker 100.

The curved bight portion 102 and legs 104 preferably lie in a common plane. However, the tips 106 extend away from the legs 104 and out of the common plane so that the tips 106 will better function as anchors for the tissue that prolapses about the tips 106 once the marker 100 is ejected from the marker recess 46 and the introducer 12 is withdrawn from the tissue mass.

Figure 12:
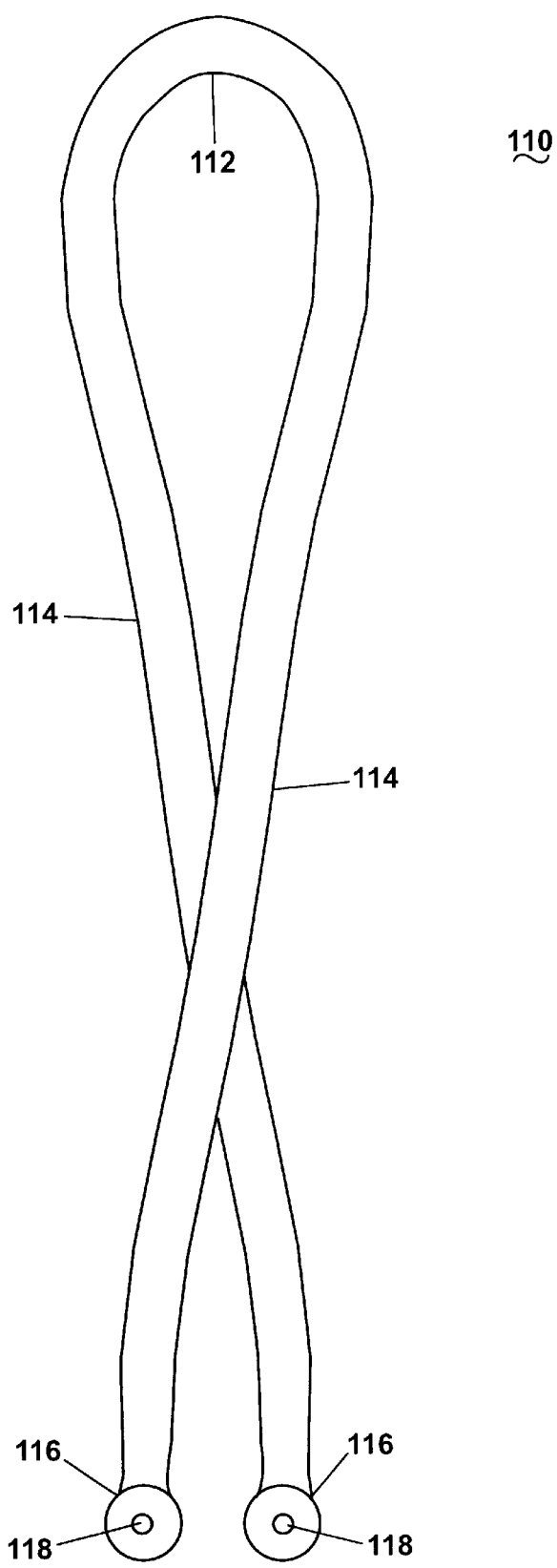
FIG. 12 is a greatly enlarged view of a sixth embodiment of a radiopaque marker according to the invention.

FIG. 12 illustrates a sixth embodiment 110 of a radiopaque marker that is similar to the horseshoe-like fifth embodiment marker 100 in that it comprises a bight portion 112 from which extend legs 114, which terminate in tips 116. The legs 114 of the marker 110 are crossed relative to each other, unlike the legs of the marker 100, providing the marker 110 with an effectively larger cross-sectional diameter. The tips 116 are oriented at approximately 90° relative to the legs 114 to form anchors. The marker 110 also has a hollow interior 118 for enhanced radiopaque characteristics.

Though, as illustrated in FIG. 12, the tips 116 of the marker 110 are oriented at approximately 90° with respect to the legs 114, it is within the scope of the invention for the tips 116 to extend at substantially any angle with respect to the legs 114. The tips 116 also need not extend away from the legs in the same direction. For example, the tips 116 could extend in opposite directions from the legs 114.

Figure 13:
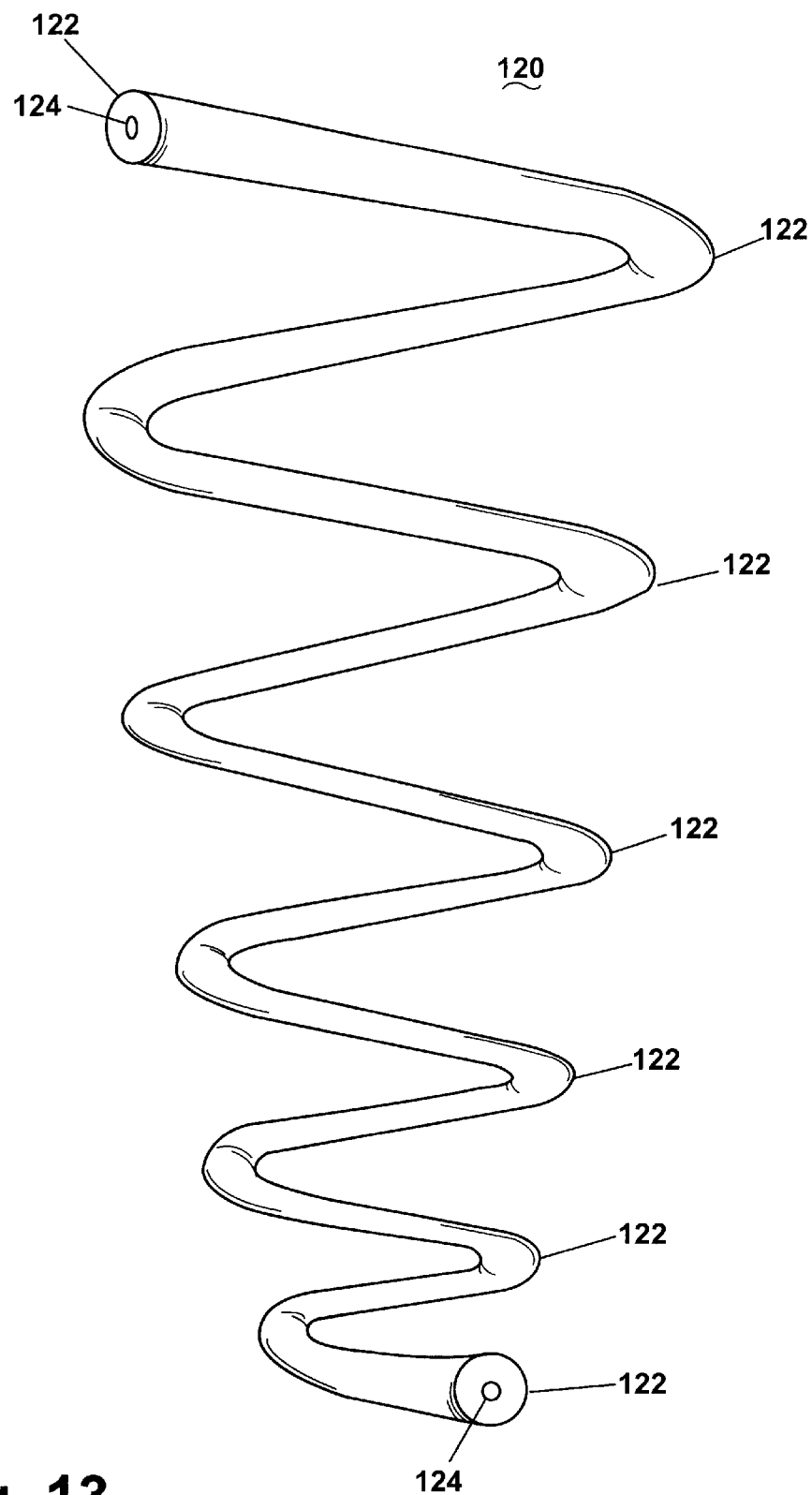
FIG. 13 is a greatly enlarged view of a seventh embodiment of a radiopaque marker according to the invention.

FIG. 13 illustrates a seventh embodiment 120 of a radiopaque marker having a generally helical configuration comprising multiple coils 122 of continuously decreasing radius. The helical marker 120 is preferably made from a radiopaque material and has a hollow interior 124 to enhance its radiopaque characteristics. The decreasing radius of the coils 122 provides the marker 120 with multiple anchor points created by the change in the effective cross-sectional diameter along the axis of the helix. In other words, since the effective cross-sectional diameter of each coil is different from the next and each coil is effectively spaced from adjacent coils at the same diametric location on the helix, the tissue surrounding the marker 120 can prolapse between the spaced coils and each coil effectively provides an anchor point against the tissue to hold the marker 120 in position and prevent its migration through the tissue mass.

Figure 14:
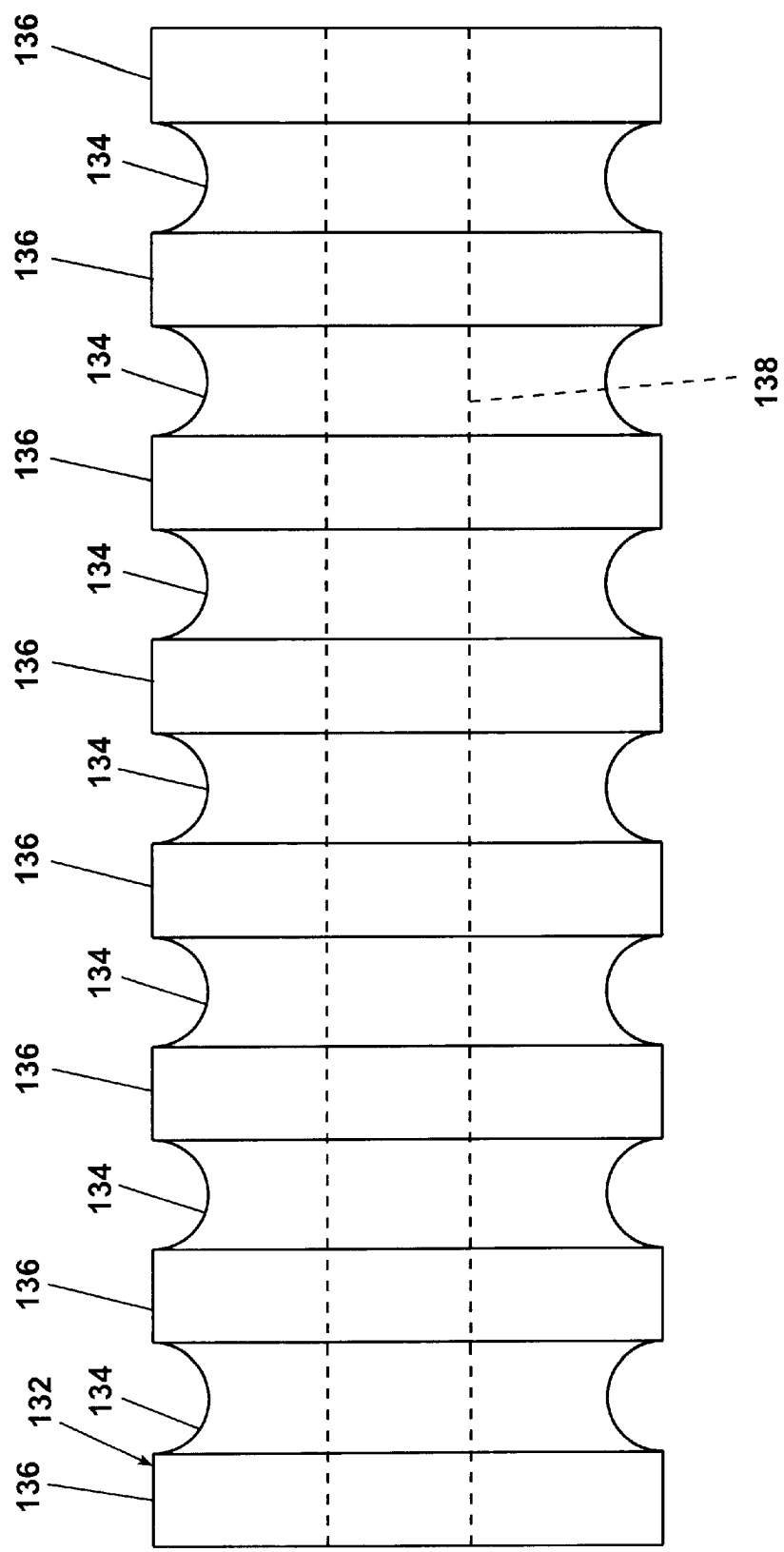
FIG. 14 is a greatly enlarged view of an eighth embodiment of a radiopaque marker according to the invention.

FIG. 14 illustrates an eighth embodiment 130 of a radiopaque marker comprising a cylindrical body 132 in which are formed a series of axially spaced circumferential grooves 134. The spaced grooves 134 form a series of ridges 136 therebetween on the outer surface of the cylindrical body 132. The cylindrical body 132 preferably includes a hollow interior 138.

The alternating and spaced ridges 136 and grooves 134 provide the marker 130 with a repeating diameter change along the longitudinal axis of the cylindrical body 132. As with the helical marker 120, the grooves 134 between the ridges 136 provide an area in which the tissue surrounding the marker 130 can prolapse thereby enveloping the ridges 136, which function as anchors for preventing the migration of the marker 130 in the tissue mass.

Figure 15:
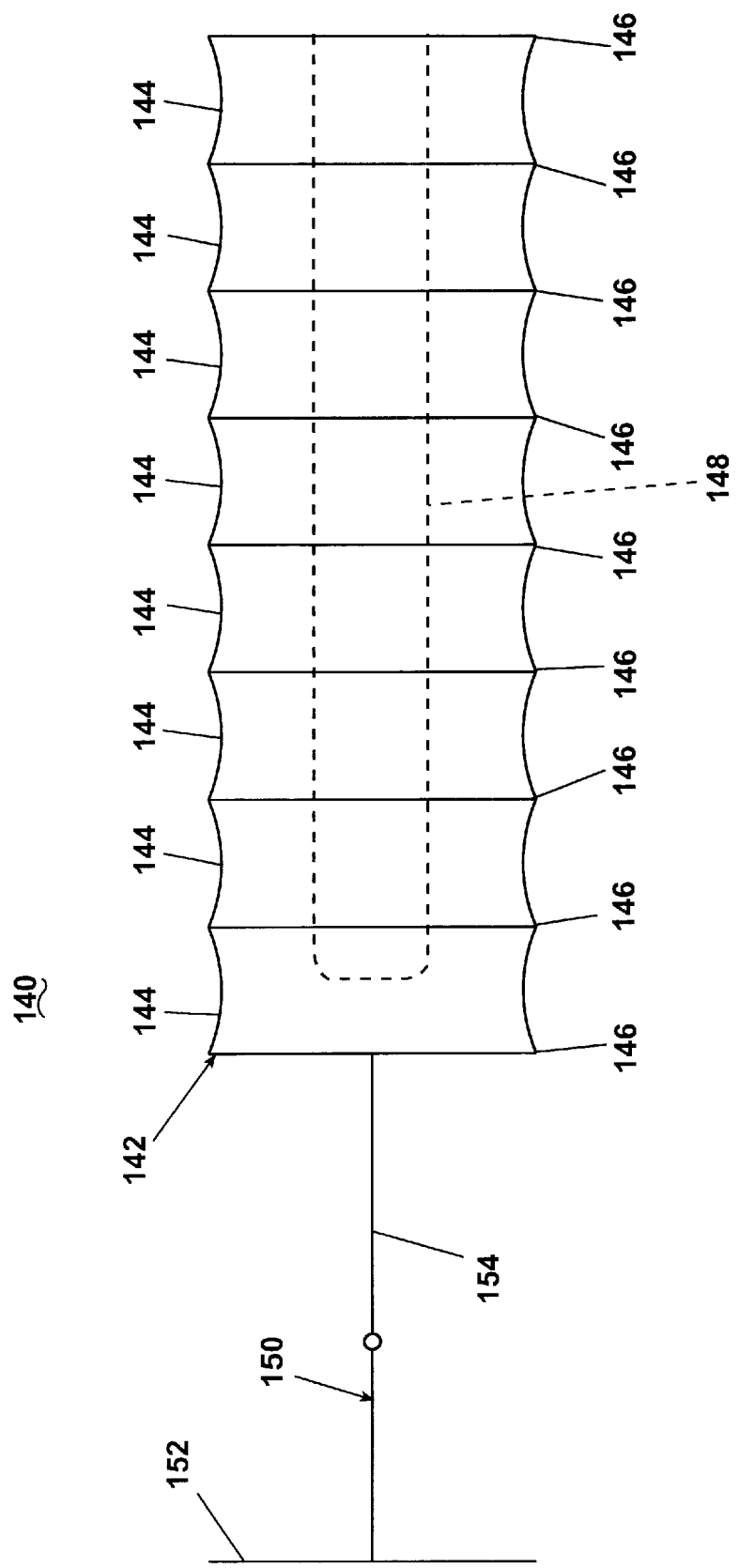
FIG. 15 is a greatly enlarged view of a ninth embodiment of a radiopaque marker according to the invention.

FIG. 15 illustrates a ninth embodiment 140 of a radiopaque marker comprising a cylindrical body 142 having an axial series of circumferential grooves 144 whose intersections with adjacent grooves form ridges 146. The cylindrical body 142 preferably includes a hollow interior 148. An anchor 150 extends from the cylindrical body 142. The anchor 150 comprises a plate 152 connected to the cylindrical body 142 by a wire 154.

The grooves 144 and ridges 146 of the maker 140 provide anchors in the same manner as the grooves 134 and ridges 136 of the marker 130. The anchor 150 further enhances the non-migrating characteristics of the marker 140 by permitting a large portion of the surrounding tissue mass to prolapse between the plate 150 and the cylindrical body 142.

The fifth through the ninth embodiments all preferably have a wire-form body. The various wire-form body shapes can be formed by stamping the shape from metal stock or the bending of a wire.

It should be noted that virtually all of the embodiments of the radiopaque marker described as being hollow can be made without a hollow interior. Similarly, those without a hollow interior can be made with a hollow interior. The hollow interior improves the ultrasound characteristics of the particular marker beyond the inherent radiopaque and ultrasound characteristics attributable to the marker shape and material. In practice, the use of the hollow interior is limited more by manufacturing and cost considerations rather than by performance.

Also, the shape of each marker can be altered to improve or enhance its non-migrating characteristics by adding an express anchor such as that disclosed in connection with the marker 140 or by modifying the marker to provide more anchor points as may be compatible with the basic configuration of the marker.

The combination of the enhanced radiopaque characteristics of the markers and the enhanced non-migrating features result in markers that are superior in use for identifying biopsy location after completion of the biopsy. The ability to accurately locate the biopsy site greatly reduces the amount of tissue that must be removed in a subsequent surgical procedure if the biopsy is cancerous. Additionally, the marker further enhances the ability to use percutaneous methods for removing the entire lesion, reducing the trauma associated with more radical surgical techniques.

The radiopaque markers described and illustrated herein are smaller than the staple-type clip and embolization coil used heretofore, thereby permitting a cannula of 14 gauge or less.

While the invention has been specifically described in connection with certain specific embodiments thereof, it is to be understood that this is by way of illustration and not of limitation, and the scope of the appended claims should be construed as broadly as the prior art will permit.

What is claimed is:

1. A biopsy marking apparatus for the percutaneous placement of a marker at a biopsy site in a tissue mass to facilitate subsequent determination of the location of the biopsy site, the biopsy marking apparatus comprising:
   an introducer having:
      a handle to be grasped by a user;
      a cannula having a proximal end mounted to the handle and a distal end defining an insertion tip,
      a stylet slidably received within the cannula for movement between a ready position in which a distal end of the stylet is spaced inwardly from the insertion tip to form a marker recess between the distal end of the stylet and the insertion tip, and an extended position in which the distal end of the stylet extends at least to the insertion tip to effectively fill the marker recess,
      a plunger movably mounted to the handle and operably engaging the stylet, the plunger being movable between a first position and a second position for moving the stylet between the ready position and the extended position, and
      a latch for fixing the stylet in the extended position to prevent retraction of the stylet from the extended position; and
   a radiopaque marker disposed within the marker recess, whereby when the plunger is moved between the first and second positions, the stylet is moved from the ready to the extended position to eject the radiopaque marker from the marker recess and the latch fixes the stylet in the extended position to prevent the return of the radiopaque marker to the marker recess.

2. The biopsy marking apparatus according to claim 1 wherein the latch comprises a detent on one of the plunger and the handle and a catch on the other of the plunger and the handle, the catch being receivable within the detent as the plunger is moved from the first to the second position.

3. The biopsy marking apparatus according to claim 2 wherein the handle defines an inner surface forming a hollow interior thereof having an open end, the plunger being slidably received within the handle hollow interior through the open end, the detent comprising a recess formed in the handle inner surface, and the catch comprising a protuberance extending from the plunger.

4. The biopsy marking apparatus according to claim 3 wherein the detent recess is spaced from the open end and the handle further comprises a groove extending from the open end to the detent recess and sized to receive the protuberance, whereby when the plunger is moved from the first to second position, the protuberance is slidably guided within the groove to the detent recess.

5. The biopsy marking apparatus according to claim 4 wherein the handle is formed with an opening extending through the handle to the inner surface to form the detent recess.

6. The biopsy marking apparatus according to claim 3 wherein the handle includes a guide passage extending from the hollow interior of the handle to the handle exterior, and the cannula proximal end is mounted within the guide passage.

7. The biopsy marking apparatus according to claim 6 wherein the stylet has a proximal end disposed within the hollow interior of the body in abutting contact with the plunger when the plunger is in the second position.

8. The biopsy marking apparatus according to claim 7 wherein the stylet proximal end includes a plate in abutting contact with the plunger when the plunger is in the second position.

9. The biopsy marking apparatus according to claim 1 wherein the radiopaque marker has an interior hollow portion thereof forming an air trap to enhance the ultrasound characteristic of the radiopaque marker.

10. The biopsy marking apparatus according to claim 9 wherein the radiopaque marker has an anchor about which a tissue mass can prolapse to aid in fixing the position of the radiopaque marker within the tissue mass.

11. The biopsy marking apparatus according to claim 1 wherein the radiopaque marker is made from a coil spring.

12. The biopsy marking apparatus according to claim 11 wherein the radiopaque marker further comprises radiopaque fibers extending from the coil spring.

13. The biopsy marking apparatus according to claim 11 wherein the radiopaque marker comprises a coil spring core and a least one coil spring finger extending from the core.

14. The biopsy marking apparatus according to claim 13 wherein there are multiple coil spring fingers extending from the core.

15. The biopsy marking apparatus according to claim 11 wherein the coil spring has a circular shape.

16. The biopsy marking apparatus according to claim 1 wherein the radiopaque marker comprises a wire-form body.

17. The biopsy marking apparatus according to claim 16 wherein the body comprises a pair of legs, each of the legs having a first end and a second end, a bight portion of the body connecting the first ends of the legs and at least one of the second ends of the legs forming an anchor.

18. The biopsy marking apparatus according to claim 17 wherein said one second end comprises a tip projecting away from a longitudinal axis of the respective leg to form the anchor.

19. The biopsy marking apparatus according to claim 18 wherein each of the second ends of the legs comprises a tip projecting away from a longitudinal axis of the respective leg to form an anchor.

20. The biopsy marking apparatus according to claim 19 wherein the tips project away from the corresponding legs in different directions.

21. The biopsy marking apparatus according to claim 17 wherein each of the legs approaches the other leg in a direction from the bight portion to the respective second end.

22. The biopsy marking apparatus according to claim 21 wherein the legs overlap.

23. The biopsy marking apparatus according to claim 16 wherein the wire-form body has a hollow interior portion forming an air trap to enhance the utrasound characteristic of the radiopaque marker.

24. The biopsy marking apparatus according to claim 1 wherein the radiopaque marker comprises a cylindrical body.

25. The biopsy marking apparatus according to claim 24 wherein the cylindrical body comprises at least one groove for receiving a portion of a tissue mass and a corresponding ridge for abutting the prolapsed tissue and thereby forming an anchor to retard the migration of the radiopaque marker within the tissue mass.

26. The biopsy marking apparatus according to claim 25 wherein there are multiple grooves and multiple corresponding ridges forming multiple anchors.

27. The biopsy marking apparatus according to claim 26 wherein the multiple grooves are continuous.

28. The biopsy marking apparatus according to claim 27 and further comprising an anchor comprising a plate and a wire connecting the plate to the cylindrical body.

29. The biopsy marking apparatus according to claim 1 wherein the maximum diameter of the cannula is 14 gauge.

30. A biopsy marking apparatus for the percutaneous placement of a marker at a biopsy site in a tissue mass to facilitate subsequent determination of the location of the biopsy site, the biopsy marking apparatus comprising:
   an elongated handle to be grasped by a user and having an opening at a first end and an inner surface defining a hollow interior connected to the opening;
   a cannula having a proximal end mounted to a second end of the handle and a distal end defining an insertion tip;
   a stylet slidably received within the cannula for movement between a ready position in which a distal end of the stylet is spaced inwardly from the insertion tip to form a marker recess between the distal end of the stylet and the insertion tip, and an extended position in which the distal end of the stylet extends toward the insertion tip to fill the marker recess a sufficient amount to expel a marker contained therein; and
   a plunger slidably received within the handle opening and operably coupled to the stylet and being moveable between a first and second position for moving the stylet between the ready position and the extended position; and
   a safety comprising a channel provided on one of the handle and the plunger and a catch provided on the other of the handle and the plunger such that when the catch and channel are aligned, the plunger can move between the first and second positions and when the catch and the channel are mis-aligned, the plunger cannot move between the first and second positions.

31. The biopsy marking apparatus according to claim 30 wherein the stylet is cylindrical.

32. The biopsy marking apparatus according to claim 30 wherein the plunger body is cylindrical.

33. The biopsy marking apparatus according to claim 30 wherein the stylet comprises a shaft and a base, with the shaft mounted to the base, the base slidably received within the hollow interior of the handle, and the shaft having a distal end forming the stylet distal end.

34. The biopsy marking apparatus according to claim 33 wherein the plunger comprises a plunger body having a lateral dimension greater than a lateral dimension of the shaft, the plunger body being coupled to the base and slidably received within the opening in the handle.

35. The biopsy marking apparatus according to claim 30 and further comprising a latch for limiting the rotation of the plunger when the plunger is in the second position.

36. The biopsy marking apparatus according to claim 35 wherein the latch comprises a recess formed in the one of the plunger and the handle and is sized to receive the catch such that the receipt of the catch in the recess limits the rotation of the plunger.

37. The biopsy marking apparatus according to claim 36 wherein the recess is located interiorly of the handle and the channel extends to the recess.

38. The biopsy marking apparatus according to claim 37 wherein the channel and the recess are provided on the handle and the catch is provided on the plunger.

39. The biopsy marking apparatus according to claim 38 wherein the handle is formed with an opening extending through the handle to the inner surface to form the recess.

40. The biopsy marking apparatus according to claim 30 and further comprising a marker disposed within the marker recess, whereby when the plunger is moved between the ready and extended positions, the stylet is moved from the ready to the extended position to eject the radiopaque marker from the marker recess.

41. The biopsy marking apparatus according to claim 40 wherein the marker is radiopaque.

42. The biopsy marking apparatus according to claim 41 wherein the handle comprises a grip portion having an enlarged diameter portion against which the user's fingers can bear to facilitate the secure gripping of the handle by the user's fingers and prevent slippage of the handle within the user's fingers, especially during the insertion of the cannula into the tissue mass.

43. The biopsy marking apparatus according to claim 42 and the handle further comprising a tapered nose portion extending from the grip portion, wherein the junction of the tapered nose portion and the grip portion define the enlarged diameter portion.

44. The biopsy marking apparatus according to claim 42 wherein the handle comprises a concave surface that terminates in a swelling to form the enlarged diameter portion.

45. The biopsy marking apparatus according to claim 44 wherein the concave surface extends around the grip portion.

46. A biopsy marking apparatus for the percutaneous placement of a marker at a biopsy site in a tissue mass to facilitate subsequent determination of the location of the biopsy site, the biopsy marking apparatus comprising:
   an elongated handle to be grasped by a user and having an opening at a first end and an inner surface defining a hollow interior connected to the opening, a cannula having a proximal end mounted to a second end of the handle, a distal end defining an insertion tip, and having a lumen opened to the hollow interior, a stylet slidably received within the cannula for movement between a ready position in which a distal end of the stylet is spaced inwardly from the insertion tip to form a marker recess between the distal end of the stylet and the insertion tip, and an extended position in which the distal end of the stylet extends toward the insertion tip to fill the marker recess a sufficient amount to expel a marker contained therein, a plunger slidably received within the handle opening and operably coupled to the stylet and being moveable between a first and second position for moving the stylet between the ready position and the extended position, and the handle comprises spaced first and second ends and a grip portion located between the spaced ends having an enlarged diameter portion against which the user's fingers can bear to facilitate the secure gripping of the handle by the user's fingers and prevent slippage of the handle within the user's fingers, especially during the insertion of the cannula into the tissue mass.

47. The biopsy marking apparatus according to claim 46 and the handle further comprising a tapered nose portion extending from grip portion, wherein the junction of the tapered nose portion and the grip portion define the enlarged diameter portion.

48. The biopsy marking apparatus according to claim 46 wherein the handle comprises a concave surface that terminates in a swelling to form the enlarged diameter portion.

49. The biopsy marking apparatus according to claim 48 wherein the concave surface extends around the grip portion.

50. The biopsy marking apparatus according to claim 46 and further comprising a safety comprising a channel provided on one of the handle and the plunger and a catch provided on the other of the handle and the plunger such that when the catch and the channel are aligned, the plunger can move between the first and second positions and when the catch and channel are mis-aligned, the plunger cannot move between the first and second positions.

51. The biopsy marking apparatus according to claim 50 and further comprising a latch for limiting the rotation of the plunger when the plunger is in the second position.

52. The biopsy marking apparatus according to claim 51 wherein the latch comprises a recess formed in the one of the plunger and the handle and is sized to receive the catch such that the receipt of the catch in the recess limits the rotation of the plunger.

53. The biopsy marking apparatus according to claim 52 wherein the recess is located interiorly of the handle and the channel extends to the recess.

54. The biopsy marking apparatus according to claim 53 wherein the channel and the recess are provided on the handle and the catch is provided on the plunger.

55. The biopsy marking apparatus according to claim 54 wherein the handle is formed with an opening extending through the handle to the inner surface to form the recess.

56. The biopsy marking apparatus according to claim 46 and further comprising a marker disposed within the marker recess, whereby when the plunger is moved between the ready and extended positions, the stylet is moved from the ready to the extended position to eject the radiopaque marker from the marker recess and the latch fixes the stylet in the extended position to prevent the return of the marker to the marker recess.

57. The biopsy marking apparatus according to claim 56 wherein the marker is radiopaque.

58. The biopsy marking apparatus according to claim 57 wherein the grip portion is longer than the nose portion.

59. The biopsy marking apparatus according to claim 58 wherein the grip portion is formed by a concave surface.

60. The biopsy marking apparatus according to claim 59 wherein the concave surface extends about the periphery of the grip portion.

\* \* \* \* \*